US009751824B2

(12) United States Patent
McGeer et al.

(10) Patent No.: US 9,751,824 B2
(45) Date of Patent: Sep. 5, 2017

(54) ACETYL SALICYCLIC ACID DIMERS, SYNTHESIS THEREOF, AND USES THEREOF TO PREVENT AND TREAT COMPLEMENT-MEDIATED DISORDERS

(71) Applicant: Aurin Biotech Inc., Vancouver (CA)

(72) Inventors: Patrick L. McGeer, Vancouver (CA); Moonhee Lee, Vancouver (CA); Edith G. McGeer, Vancouver (CA)

(73) Assignee: Aurin Biotech Inc., Vancouver, BC ( * ) Notice: Subject to any disclaimer, the term of this patent is extended or adjusted under 35 U.S.C. 154(b) by 0 days.

(21) Appl. No.: 15/036,212

(22) PCT Filed: Nov. 17, 2014

(86) PCT No.: PCT/CA2014/051097
§ 371 (c)(1),
(2) Date: May 12, 2016

(87) PCT Pub. No.: WO2015/070354
PCT Pub. Date: May 21, 2015

(65) Prior Publication Data
US 2016/0297743 A1 Oct. 13, 2016

Related U.S. Application Data

(60) Provisional application No. 61/905,596, filed on Nov. 18, 2013.

(51) Int. Cl.
*A61K 31/225* (2006.01)
*C07C 69/16* (2006.01)
(Continued)

(52) U.S. Cl.
CPC .............. *C07C 69/16* (2013.01); *A61K 8/375* (2013.01); *A61K 9/0014* (2013.01); *A61Q 5/006* (2013.01);
(Continued)

(58) Field of Classification Search
CPC ..... C07C 69/16; C07C 69/017; A61Q 19/008; A61Q 5/006; A61Q 19/004; A61Q 7/00; A61K 8/375; A61K 9/0014
(Continued)

(56) References Cited

U.S. PATENT DOCUMENTS 3,515,695 A * 6/1970 Loughran ............ C08G 63/065
524/601
4,007,270 A 2/1977 Bernstein
(Continued)

FOREIGN PATENT DOCUMENTS

CA 1086743 9/1980
CA 2284620 A1 10/1988
(Continued)

OTHER PUBLICATIONS

Anastasiou, Theodore J., et al, "Syntheses of aminosalicylate-based polyanhydride produgs: esters, amides, and azos", Polymer Prepreints, 2001, 42(2):121-122.
(Continued)

*Primary Examiner* — T. Victor Oh
(74) *Attorney, Agent, or Firm* — Oyen Wiggs Green & Mutala LLP

(57) ABSTRACT

Dimers of acetyl salicylic acid, including 4,4'-diacetoxy-[1, 1'-biphenyl]-3,3'-dicarboxylic acid (DAS-1) and 5,5'-methylenebis(2-acetoxybenzoic acid) (DAS-2) are provided. Methods of blocking the C3 convertase stage of the alternative complement pathway, preventing formation of the membrane attack complex of complement, and preventing or treating a complement-mediated disorder in a mammal including the step of administering dimers of acetyl salicylic acid are also provided.

4 Claims, 9 Drawing Sheets

(51) Int. Cl.
*A61K 9/00* (2006.01)
*A61K 8/37* (2006.01)
*A61Q 5/00* (2006.01)
*A61Q 7/00* (2006.01)
*A61Q 19/00* (2006.01)
*C07C 69/017* (2006.01)

(52) U.S. Cl.
CPC ............. *A61Q 7/00* (2013.01); *A61Q 19/004* (2013.01); *A61Q 19/008* (2013.01); *C07C 69/017* (2013.01)

(58) Field of Classification Search
USPC .................................................. 514/548, 547
See application file for complete search history.

(56) References Cited

U.S. PATENT DOCUMENTS

| | | |
|---|---|---|
| 4,123,455 A | 10/1978 | Conrow |
| 5,030,442 A | 7/1991 | Uster |
| 2013/0035388 A1 | 2/2013 | McGeer |
| 2014/0163106 A1 | 6/2014 | McGeer |

FOREIGN PATENT DOCUMENTS

| | | |
|---|---|---|
| GB | 723525 | 2/1955 |
| WO | 2014009779 A1 | 1/2014 |
| WO | 2014085920 A1 | 6/2014 |

OTHER PUBLICATIONS

Anderson, D.H., et al, "The pivotal role of the complement system in aging and age-related macular degeneration: hypothesis revisited", Prog Ret Eye Res, 2010, 29:95-112.
Ballanti E, et al, "Role of the complement system in rheumatoid arthritis and psoriatic arthritis: relationship with anti-TNF inhibitors", Autoimmun Rev, 2011, 10(10):617-623.
Garza, LA, et al, "Prostaglandin D2 inhibits hair growth and is elevated in bald scalp of men with androgenic alopecia", Sci Transl Med, 2012, 4:126.
Harries, MJ, et al, "Hair loss as a result of cutaneous autoimmunity: frontiers in the immunopathogenesis of primary cicatricial alopecia", Autoimmune Rev., 2009, 8(6):478-483.
Harries, MJ, et al, "Does collapse of immune privilege in the hair-follicle bulge play a role in the pathogenesis of primary cicatricial alopecia?", Clin Exp Dermatol, 2010, 35(6):637-644.
Hillmen, P, et al, "The complement inhibitor eculizumab in paroxysmal nocturnal hemoglobinuria", N Engl J Med, 2006, 355:1233-1243.
Hillmer, AM, et al, "Genetic variation in the human androgenic receptor gene is the major determinant of common early-onset androgenic alopecia", Am J Hum Gen, 2005, 77(1):140-148.
Jokiranta, TS, et al, "Structure of complement factor H carboxyl terminus reveals molecular basis of atypical haemolytic uremic syndrome", EMBO Journal, 2006, 25:1784-1794.
Kawana, S, et al, "Deposition of the membrane attack complex of complement in pemphigus vulgaris and pemphigus foliaceus skin", J Investig Dermatol, 1989, 92(4):588-592.
Kerr, K, et al, "Epidermal changes are associated with symptomatic resolution of dandruff: biomarkers of scalp health", Int J Dermatol, 2011, 50(1):102-113.
Knor, T, "The pathogenesis of acne", Acta Dermatovenerol Croa, 2005, 13(1):44-49.
Meyer, KC, et al, "Evidence that the bulge region is a site of relative immune privilege in human hair follicles", Br J Dermatol, 2008, 159(5):1077-1085.
Mills, KJ, et al, "Dandruff/seborrhoeic dermatitis is characterized by an inflammatory genomic signature and possible immune dysfunction: transcriptional analysis of the condition and treatment effects of zinc pyrithione", Br J Dermatol, 2012,166 Suppl 2, 33-40.
Okroj M, "Rheumatoid arthritis and the complement system", Ann. Med., 2007, 39, 517-530.
Parker, CJ, "Historical aspects of paroxysmal nocturnal haemoglobinuria: defining thed disease", Br J Haematol, 2002, 117:3-22.
Prodi DA, et al, "EDA2R is associated with androgenic alopecia", J Inves Derm, 2008, 128:2268-2270.
Rogers, J, et al. "Complement activation by b-amyloid in Alzheimer disease", PNAS USA, 1992, 89:10016-10020.
Schwartz, JR, et al, "A comprehensive pathophysiology of dandruff and seborrheic dermatitis—towards a more precise definition of scalp health", Acta Derm Venereol, 2013, 93(2):131-137.
Seah, PP, et al, "Alternate-pathway complement fixation by IgA in the skin of dermatitis herpetiformis", Lancet, 1973, 175-177.
Silver, KL, et al, "Complement driven innate immune response to malaria: fuelling severe malarial diseases", Cell Microbiol, 2010, 12(8):1036-1045.
Triolo, G, et al, "Impaired expression of erythrocyte glycolphosphotidylinosotol-anchored membrane CD59 in patients with psoriatic arthritis. Relation to terminal complement pathway activation", Clin Exp Rheumatol, 2003, 21; 225-228.
Wan, KC, et al, "A longitudinal study of C3, C3d, and Factor Ba in burn patients in Hong Kong Chinese", Burns, 1998, 24(3):241-244.
Yasojima, K, et al, "Generation of C-reactive protein and complement components in atherosclerotic plaques", Am J Pathol, 2001, 158:1038-1051.

* cited by examiner

3',4-diacetoxy-[1,1'-biphenyl]-3,4'-dicarboxylic acid
para-meta DAS-1

2,4'-diacetoxy-[1,1'-biphenyl]-3,3'-dicarboxylic acid
para-ortho DAS-1

2,3'-diacetoxy-[1,1'-biphenyl]-3,4'-dicarboxylic acid
meta-ortho DAS-1

3,3'-diacetoxy-[1,1'-biphenyl]-4,4'-dicarboxylic acid
meta-meta DAS-1

2,2'-diacetoxy-[1,1'-biphenyl]-3,3'-dicarboxylic acid
ortho-ortho DAS-1

2-acetoxy-4-(4-acetoxy-3-carboxybenzyl)benzoic acid
para-meta DAS-2

2-acetoxy-3-(4-acetoxy-3-carboxybenzyl)benzoic acid
para-ortho DAS-2

3,3'-methylenebis(2-acetoxybenzoic acid)
ortho-ortho DAS-2

2-acetoxy-3-(3-acetoxy-4-carboxybenzyl)benzoic acid
ortho-meta DAS-2

4,4'-methylenebis(2-acetoxybenzoic acid)
meta-meta DAS-2

ACETYL SALICYCLIC ACID DIMERS, SYNTHESIS THEREOF, AND USES THEREOF TO PREVENT AND TREAT COMPLEMENT-MEDIATED DISORDERS

TECHNICAL FIELD

The present invention pertains to dimers of acetyl salicylic acid, synthesis of such dimers, and use of such dimers to prevent and treat complement-mediated disorders.

BACKGROUND

Mammals are equipped with a powerful innate immune system to ward off challenges from the external environment. Complement is a vital component of that immune protection. However, complement is a two-edged sword because aberrant complement activation can also damage host tissue. For example, complement activation which exceeds the limitations of the host's protective systems can result in self-damage to viable host tissue.

It would be beneficial to have novel inhibitors of the complement system for use as regulators of aberrant complement activation and/or as therapeutics in the prophylaxis and/or treatment of complement-mediated disorders.

SUMMARY

One aspect of the invention provides a compound, namely a dimer of acetyl salicylic acid, or a salt thereof. In some embodiments, the dimer may be selected from the group consisting of 4,4'-diacetoxy-[1,1'-biphenyl]-3,3'-dicarboxylic acid (DAS-1) and its isomers, namely 2,4'-diacetoxy-[1,1'-biphenyl]-3,3'-dicarboxylic acid, 3,3'-diacetoxy-[1,1'-biphenyl]-4,4'-dicarboxylic acid, 3,4'-diacetoxy-[1,1'-biphenyl]-3,4'-dicarboxylic acid, 2,3'-diacetoxy-[1,1'-biphenyl]-3,4'-dicarboxylic acid, 2,2'-diacetoxy-[1,1'-biphenyl]-3,3'-dicarboxylic acid, and salts thereof. In a preferred embodiment, the dimer may be 4,4'-diacetoxy-[1,1'-biphenyl]-3,3'-dicarboxylic acid (DAS-1), or a salt thereof. In other embodiments, the dimer may be selected from the group consisting of 5,5'-methylenebis(2-acetoxybenzoic acid) (DAS-2), and its isomers, namely 2-acetoxy-3-(4-acetoxy-3-carboxybenzyl)benzoic acid, 2-acetoxy-3-(3-acetoxy-4-carboxybenzyl)benzoic acid, 2-acetoxy-4-(4-acetoxy-3-carboxybenzyl)benzoic acid, 3,3'-methylenebis(2-acetoxybenzoic acid), 4,4'-methylenebis(2-acetoxybenzoic acid), and salts thereof. In another preferred embodiment, the dimer may be 5,5'-methylenebis(2-acetoxybenzoic acid) (DAS-2), or a salt thereof.

Another aspect of the invention provides a pharmaceutical composition comprising a dimer of acetyl salicylic acid, such as DAS-1 and DAS-2 or their isomers and a pharmaceutically acceptable carrier. In some embodiments, the composition is essentially free of monomers and non-dimer multimers of acetyl salicylic acid.

Another aspect of the invention provides a method of blocking the C3 convertase stage of the alternative complement pathway, the method comprising administering an effective amount of a dimer of acetyl salicylic acid, such as DAS-1 and DAS-2 or their isomers.

Another aspect of the invention provides a method of preventing formation of the membrane attack complex of complement, the method comprising administering an effective amount of a dimer of acetyl salicylic acid, such as DAS-1 and DAS-2 or their isomers.

Another aspect of the invention provides a method of preventing or treating a complement-mediated disorder in a mammal, the method comprising administering to the mammal an effective amount of a dimer of acetyl salicylic acid, such as DAS-1 and DAS-2 or their isomers.

Another aspect of the invention provides a method of preventing or treating a complement-mediated disorder in a mammal, wherein the disorder is a chronic inflammatory disease, the method comprising administering to the mammal an effective amount of a dimer of acetyl salicylic acid, such as DAS-1 and DAS-2 or their isomers. In example embodiments, the disorders include chronic inflammatory and/or degenerative conditions such as, paroxysmal nocturnal hemoglobinemia, age related macular degeneration, Alzheimer's disease, rheumatoid arthritis, atherosclerosis, atypical hemolytic uremia syndrome, multiple sclerosis, malaria infection, Pick's disease, Parkinson's disease, and neuromyelitis optica. In some embodiments, the administration step includes oral administration. In some embodiments, the methods exclude administration of monomers and non-dimer multimers of acetyl salicylic acid.

Another aspect of the invention provides a method of preventing or treating a complement-mediated disorder in a mammal, wherein the disorder is an inflammatory skin disease, the method comprising administering to the mammal an effective amount of a dimer of acetyl salicylic acid, such as DAS-1 and DAS-2 or their isomers. In example embodiments, the diseases include androgenetic alopecia, thermal or ultraviolet burn, acne, atopic dermatitis, dandruff/seborrheic dermatitis, pemphigus, erythematosis, cicatricial alopecia and alopecia areata. In some embodiments, the administration step includes topical administration. In some embodiments, the methods exclude administration of monomers and non-dimer multimers of acetyl salicylic acid.

These and other aspects of the invention will become evident upon reference to the following drawings and detailed description.

BRIEF DESCRIPTION OF DRAWINGS

In drawings which show non-limiting embodiments of the invention:

FIG. 4A shows that DAS-1 and DAS-2 do not block the opsonizing steps. FIG. 4B shows that DAS-1 and DAS-2 block at the stage where C9 binds to C5b678.

FIG. 5 shows that DAS-1 and DAS-2 block occurs at the stage where membrane-bound PC3bB is cleaved by Factor D. Factor D does not bind to the complex but remains in solution.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

The term "chronic inflammatory disease" refers to diseases or conditions characterized by persistent inflammation, typically in the absence of an identifiable irritant or microbial pathogen.

The term "complement-mediated disorder" as used herein refers to a disorder in which its pathogenesis involves complement activation which exceeds a subject's self-protective mechanisms (such as self-protective proteins including CD 55 (decay accelerating factor), CD 59 (protectin), Factor H, and the like) and causes self-damage to the subject's tissue.

The term an "effective amount" as used herein refers to the amount of the active agent sufficient to elicit a desired biological response (or, equivalently, to inhibit an undesired biological response). As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses.

The term "mammal" refers to any mammalian species including without limitation mice, rats, rabbits, dogs, primates and, in particular, humans.

The term "prevent" and "preventing" as used herein refers to arrest, delay of onset (i.e., the period prior to clinical manifestation of a disease or condition) and/or reduction of the risk of developing or worsening a disease or condition in a subject.

The term "subject" as used herein, refers to an individual to whom an agent is to be delivered, e.g., for prophylactic or therapeutic purposes. Preferred subjects are mammals, including humans and domesticated mammals.

The term "treat", "treating" and "treatment" as used herein refers to relief, reduction or alleviation of at least one symptom of a disease or condition in a subject. For example, treatment can be diminishment of one or several symptoms of a disease or condition or complete eradication of a disease or condition.

Figure 2A:
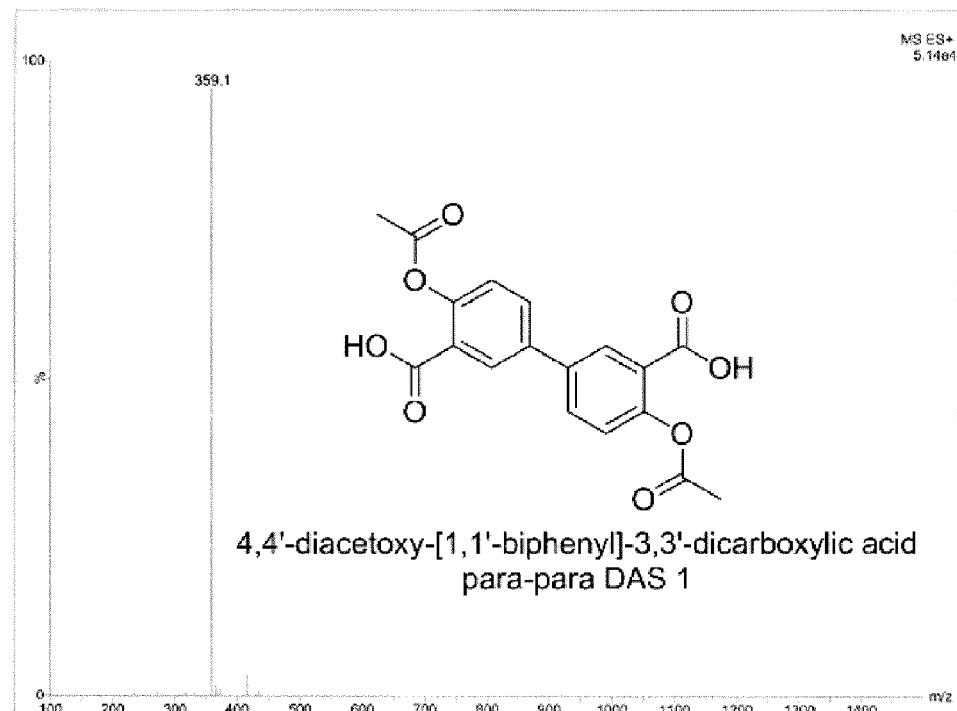
FIGS. 2A and 2B show mass spectrographic analysis of DAS-1 and DAS-2, respectively, along with their structures and formal names. Mass spectroscopy was run in the +1 mode so that the apparent masses of DAS-1 at 359 and DAS-2 at 373 are +1 greater than their true mass of 358 and 372 respectively.
Figure 2B:
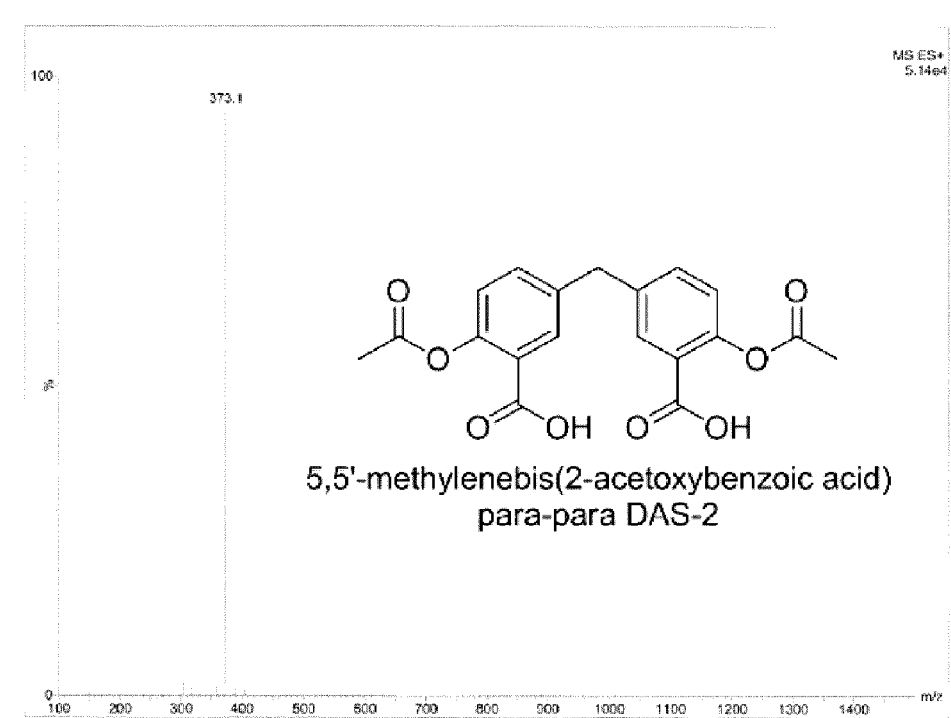
Figure 2C:
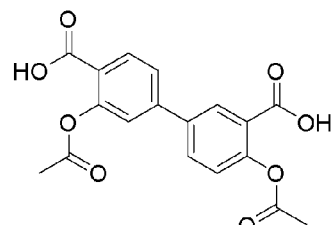
FIG. 2C shows structures of isomers of DAS-1 which includes the para-meta, para-ortho, meta-meta, meta-ortho, and ortho-ortho forms along with their proper chemical names.
Figure 2C:
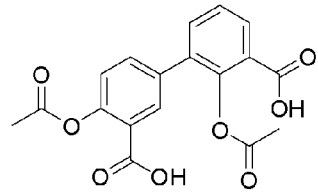
Figure 2C:
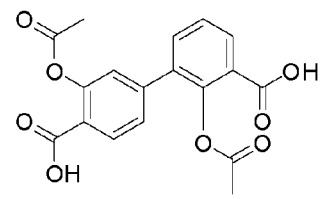
Figure 2C:
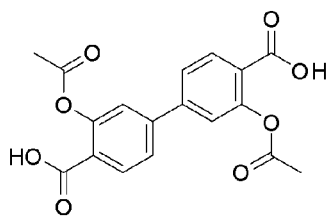
Figure 2C:
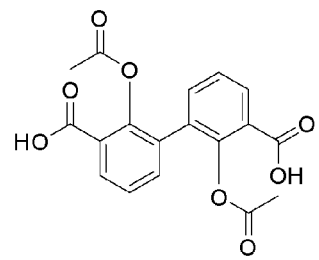

One aspect of the invention provides a compound which is a dimer of acetyl salicylic acid. In one embodiment, the compound is 2,2'diacetoxy-4,4'biphenyl carboxylic acid, herein described as diacetyl salicylic acid-1 (DAS-1). DAS-1 has a structure which is shown in FIG. 2A. DAS-1 is the para-para form. Other embodiments include isomers of DAS-1 in the para-meta, para-ortho, meta-meta, meta-ortho, and ortho-ortho forms as shown in FIG. 2C.

Figure 2D:
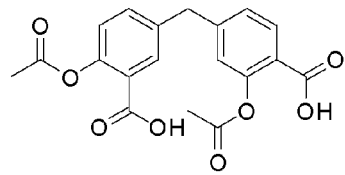
FIG. 2D shows structures of the isomers of DAS-2 which includes the para-meta, para-ortho, meta-meta, meta-ortho, and ortho-ortho forms along with their proper chemical names.
Figure 2D:
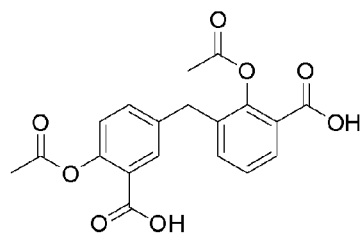
Figure 2D:
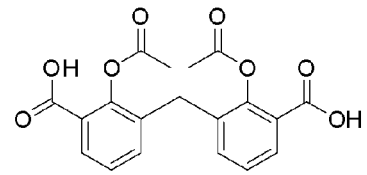
Figure 2D:
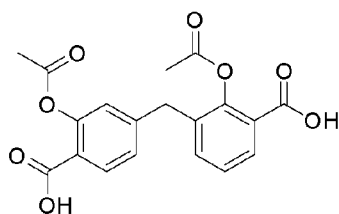
Figure 2D:
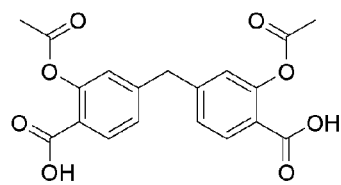

In another embodiment, the compound is 4,4'-methylenebis-(2-acetoxybenzoic acid), herein described as diacetyl salicylic acid-2 (DAS-2). DAS-2 has a structure which is shown in FIG. 2B. DAS-2 is the para-para form. Other embodiments include isomers of DAS-2 in para-meta, para-ortho, meta-meta, meta-ortho, and ortho-ortho forms as shown in FIG. 2D.

Example Synthesis and Separation of DAS-1 and DAS-2

Synthesis of diacetylsalicylic acid-1 (DAS-1) and diacetylsalicylic acid-2 (DAS-2) has not been previously described. The following procedure is an example embodiment for DAS-2. 3-chloro-2-hydroxybenzoic acid is dissolved in 1 mmol per mL of methanol. A 25% volume of water is added, and the solution cooled to 0° C. A volume of concentrated sulfuric acid equal to 3 times the volume of methanol is added dropwise. To this solution a volume of 37% w/v aqueous solution of formaldehyde equal to 40% of the volume of methanol is added dropwise. The solution is stirred at 0° C. for one hour, and then warmed to room temperature and stirred for 48 hrs. The solution is then poured over crushed ice (100 g of ice per 1 g of 3-chloro-2-hydroxybenzoic acid). The precipitate is then filtered and rinsed with ice cold water. The crude product is purified by silica gel chromatography using a mixture of chloroform, tetrahydrofuran and formic acid as the eluant. The product is then dried under vacuum. $^1$HNMR (400 MHz, acetone-$d_6$): δ 7.78 ppm (d, 2H, J=2.25 Hz), 7.60 ppm (d, 2H, J=2.25 Hz), 3.99 ppm (s, 2H). $^{13}$C NMR (100.6 MHz, acetone-$d_6$) δ 72.28, 157.13, 137.02, 133.22, 129.85, 122.37, 114.61, 39.43 ppm. The product is dissolved in ethanol such that the concentration is equal to 5 mmol per 30 mL. A volume of triethylamine equal to 50% of the volume of ethanol is then added to the solution. Palladium on carbon (5%, 30 mg per 1 g of 5,5'-methylenebis(3-chloro-2-hydroxybenzoic acid) is then added, and the solution is stirred under an atmosphere of hydrogen at room temperature for 48 hours. The catalyst is then filtered off, the solvent evaporated and a volume of water (55 mL per 1 g of product) is added. The solution is cooled and then acidified by addition of concentrated hydrochloric acid. The precipitate is then filtered off and rinsed with ice cold water. $^1$HNMR (300 MHz, acetone-$d_6$): δ 7.77 ppm (d, 2H, J=2.25 Hz), 7.42 ppm (dd, 2H, J=8.55 Hz and 2.25 Hz), 6.90 ppm (d, 2H, J=8.55 Hz), 3.95 ppm (s, 2H). $^{13}$C NMR (100.6 MHz, acetone-$d_6$) δ 72.59, 161.36, 137.23, 133.04, 130.95, 118.15, 113.27, 40.13 ppm. The product (0.1 g) was dissolved in 5 mL of acetic anhydride (Sigma). 4-(N,N-dimethylamino)pyridine (DMAP, 0.03 grams, Sigma) was added to the mixture. Acetylation reaction was performed at room temperature for 24 h on the magnetic stirrer. Crushed ice (50 g) was added. Ethyl acetate (20 mL)

was added to the reaction mixture, which was then left in room temperature for 30 min. The upper layer (ethyl acetate layer) was collected and washed with deionized water 3 times. The ethyl acetate layer was collected and dried at room temperature for 24 h. $^1$HNMR (300 MHz, acetone-$d_6$): δ 7.98 ppm (d, 2H, J=2.21 Hz), 67.54 ppm (dd, 2H, J=8.25 Hz and 2.21 Hz), δ 7.12 ppm (d, 2H, J=8.25 Hz), 64.16 ppm (s, 2H), 62.22 ppm (s, 6H). This analysis demonstrated 95% purity of DAS-2.

A further embodiment suitable for synthesis and separation of DAS-1 and DAS-2 is as follows.

Approximately 70 mL of sulfuric acid ($H_2SO_4$) is poured into a beaker on ice. Approximately 10 grams of sodium nitrite ($NaNO_2$) is added. In some embodiments, the sodium nitrite is added in a portion-wise manner over an approximately 30 minute period. In some embodiments, the temperature of the reaction mixture is less than 5° C. Next, approximately 20 grams of acetyl salicylic acid (ASA) is added. In some embodiments, the addition of ASA is in a portion-wise manner over a 20 minute period while stirring. Next, 30% formaldehyde solution is added in a drop-wise manner. In some embodiments, the formaldehyde solution is added over an approximately 30 minute period. In some embodiments, the temperature of the reaction mixture is less than 5° C. Next, approximately 200 gram of ice is added directly to the beaker, followed by the addition of approximately 300 mL of cold water. The reaction mixture is stirred for 18 h at room temperature. The resulting light brown powder is separated by filtration and dried. To separate the products, dissolve the powder in methanol. The solution (4.5 mg in 1 mL) can then be loaded onto a size exclusion chromatography column (Sephadex LH-20, GE healthcare, Piscataway, N.J., packed in 60% methanol). Two eluant fractions can be collected. They can be analyzed by mass spectrometry on a Waters ZQ apparatus equipped with an ESCI ion source and a Waters Alliance Quadrupole detector. Separation of the DAS-1 and DAS-2 products can be verified by this procedure.

In some embodiments, the foregoing methods may be scaled up for volume production.

The Complement System

Figure 1:
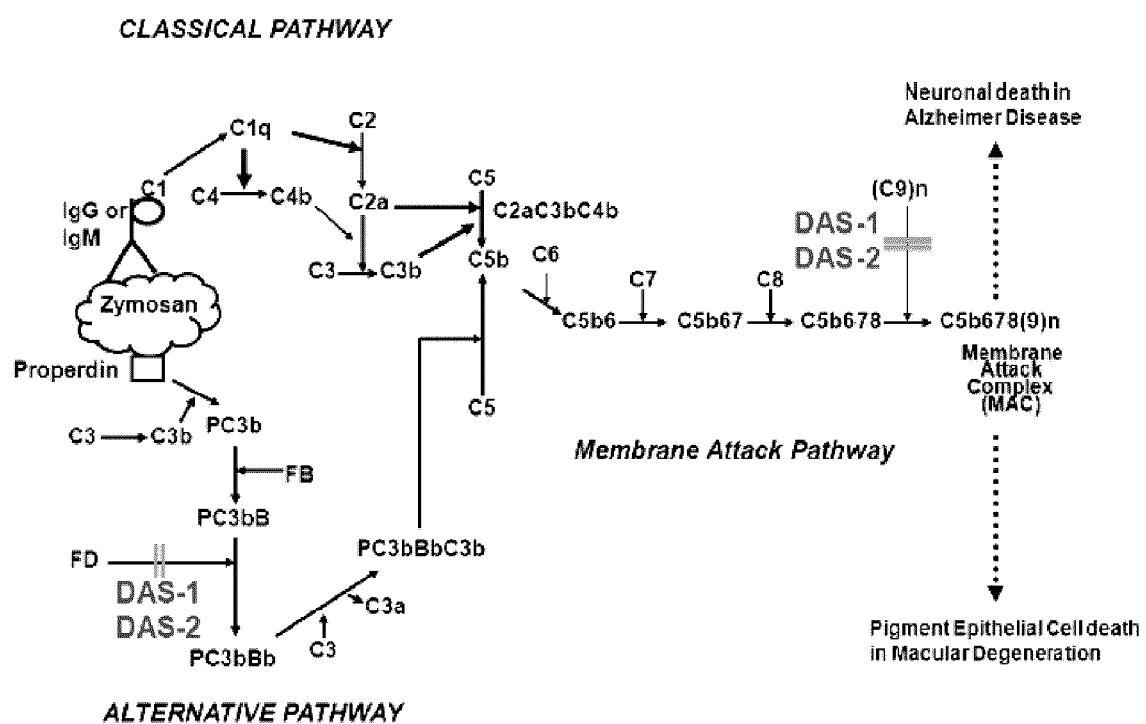
FIG. 1 is a schematic diagram showing the sequence of reactions in the classical and alternative complement pathways. The steps blocked by dimers of acetyl salicylic acid, DAS-1 and DAS-2, are shown. For both pathways, the step of insertion of C9 into C5b678 is blocked. For the alternative pathway the step of cleavage of PC3bB by Factor D is blocked.

As shown in FIG. 1, the complement system consists of two main pathways: the classical and the alternative. The pathways have differing opsonizing mechanisms, but they have in common assembly of the terminal components to form the membrane attack complex (C5b-9). There are numerous ways by which the pathways may become activated. Zymosan, a glucan found on the surface of fungi, is used as a standard activator for many types of experimental assays. It induces activation of the classical pathway where a target can be presented that needs to be phagocytosed. The C1q component of the C1 complex recognizes zymosan. Subsequent steps are then induced, which involve dissociation of the C1 complex, cleavage of C2, C4, and C3 to provide amplification as well as covalent attachment of the activated complement components to the target. By this means the target can be disposed of by phagocytes that have receptors for the activated complement components so attached. The alternative pathway can also be induced. In this pathway, properdin (P) binds to the target causing soluble C3b to bind as well. Then factor B binds to the complex. Soluble Factor D then cleaves bound Factor B to form the highly active PC3bBb, which immediately cleaves more C3, creating PC3bBbC3b, also known as C3 convertase.

Both pathways result in C5 being cleaved into C5a and C5b. The released C5b fragment can then insert itself into the membranes of nearby cells. C6, C7, C8 and C9 (n) can then become sequentially attached to the membranes. The addition of C9 renders the complex functional by opening holes in the membranes, thus leading to death of the cells. Its physiological purpose is to kill foreign pathogens, but over-activation can result in destruction of host cells by a phenomenon known as bystander lysis.

The complement system therefore operates in two parts. The first part is opsonization, which prepares targeted tissue for phagocytosis. The second part is assembly of the membrane attack complex, which has the purpose of killing cells. The former is essential, but the latter is not. For example, approximately 0.12% of Japanese are homozygous for the nonsense CGA-TGA (arginine 95 stop) mutation in exon 4 of C9. These individuals cannot make a functioning membrane attack complex. This means that there are more than 150,000 Japanese leading healthy lives despite this deficiency. The same mutation is found in about 0.16% of Koreans, indicating that there are about 40,000 people in the Republic of Korea also leading healthy lives. The inventors have therefore determined from the Japanese and Korean experience that selective inhibition of membrane attack complex formation on a long term basis is a viable therapeutic strategy.

The membrane attack complex exacerbates the pathology in all diseases where aberrant complement activation occurs. Relevant chronic inflammatory and/or degenerative diseases include, but are not limited to, rheumatoid arthritis, paroxysmal nocturnal hemoglobinemia, atypical hemolytic uremia syndrome, multiple sclerosis, neuromyelitis optica, malaria infection, Alzheimer disease, age related macular degeneration, Parkinson's disease, Pick's disease, amyotrophic lateral sclerosis and atherosclerosis. Relevant inflammatory skin diseases include, but are not limited to, androgenetic alopecia (baldness), acne, thermal or ultraviolet burns, atopic dermatitis, seborrheic dermatitis/dandruff, primary cicatricial alopecia, pemphigus, psoriasis, discoid lupus erythematosis, and dermatitus herpetiformis.

DAS-1 and DAS-2 as Selective Inhibitors of the Membrane Attack Complex and C3 Convertase As discussed above, complement activation which exceeds the limitations of the host's protective systems can result in self-damage to viable host tissue. The inventors have discovered that dimers of acetylsalicylic acid, but not acetylsalicylic acid itself, confer protection against such self-damage. Dimers of acetylsalicylic acid, such as DAS-1 and DAS-2, do so by blocking unwanted C3 convertase activity of the alternative pathway, as well as unwanted MAC assembly at the final stage of C9 addition to C5b678 of both the alternative and classical pathways, as shown in FIG. 1.

The structure and molecular weight (MW) of DAS-1 and DAS-2 according to example embodiments are shown in FIGS. 2A and 2B. FIG. 2A shows the structure of DAS-1 ($C_{18}$, $H_{14}$, $O_8$) and the match between that structure and the molecular weight of the synthesized product as determined by mass spectrographic analysis. The analysis was run in the +1 mode giving a value +1 (359) above the actual MW of 358. FIG. 2B gives similar data for DAS-2 ($C_{19}$, $H_{16}$, $O_9$) showing its MW by mass spectrographic analysis in the +1 mode giving a value of 373 which is +1 above the actual MW weight of 372.

To evaluate the strength of blockade of the classical complement pathway achieved by DAS-1 and DAS-2, a standard CH50 assay was employed. Normal human red blood cells were sensitized by incubation overnight with rabbit anti red blood cell antibody. Then dilutions of serum activated by zymosan, with and without various amounts of DAS-1, DAS-2, or the precursor acetylsalicylic acid, were incubated with the sensitized red blood cells for 1 hour at 37° C. The incubates were centrifuged at 5,000 rpm for 10 min. The hemoglobin released into the serum from red blood cells that had been destroyed by complement attack, was determined by reading the optical density (OD) at 405 nm. As a positive control, red blood cells were 100% lysed with water, and as a negative control, no serum was added to the incubate.

Figure 3A:
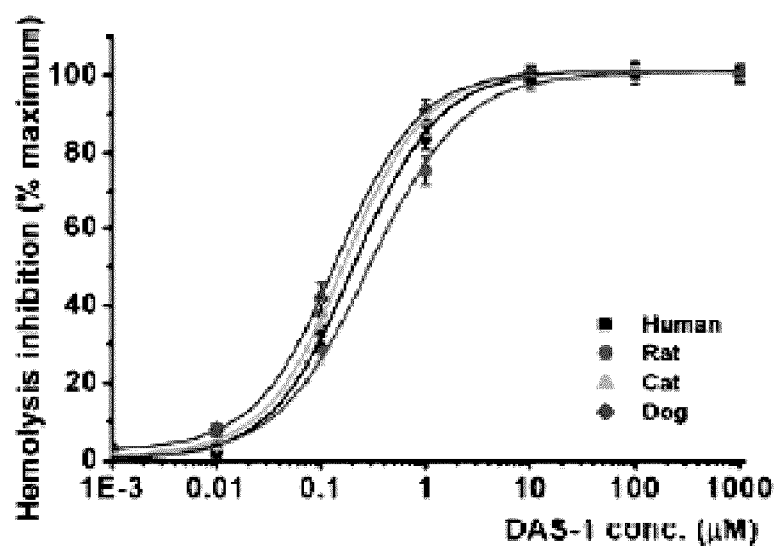
FIGS. 3A to 3C are graphs showing CH50 analyses of human red cell hemolysis by zymogen-activated serum from human, rat, cat, and dog. The degree of protection of such hemolysis by DAS-1 (FIG. 3A), and DAS-2 (FIG. 3B) is shown along with their IC50s. The precursor acetyl salicylic acid (FIG. 3C) confers no protection even at 10,000 times higher concentrations.
Figure 3B:
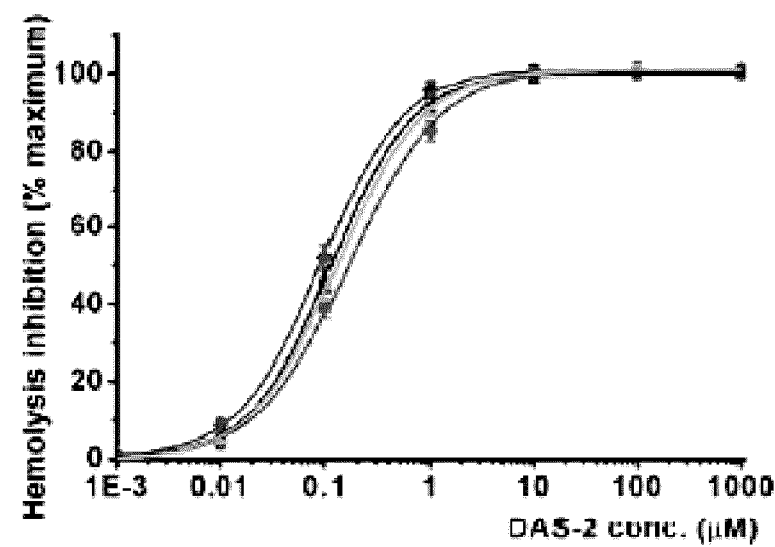
Figure 3C:
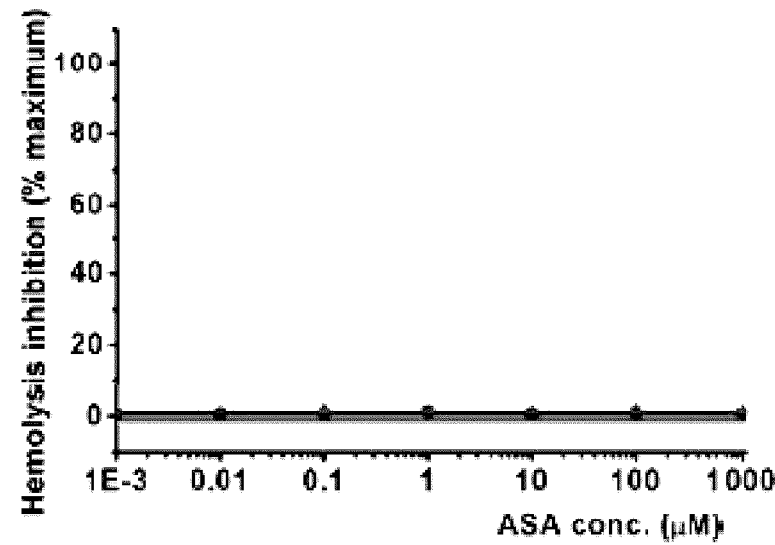

The results are shown in FIG. 3. DAS-1 and DAS-2 protected human red blood cells from complement attack by zymogen activated serum of human, rat, cat, and dog. FIG. 3A illustrates the result for DAS-1. $IC_{50}$ values were 208 nM for human, 294 nM for rat, 168 nM for cat, and 142 nM for dog serum. FIG. 3B illustrates comparable data for DAS-2. $IC_{50}$ values of serum were 113 for human, 167 for rat, 128 for cat and 98 for dog. FIG. 3C shows that the precursor, acetylsalicylic acid, gave no protective effect even when added at 1 mM, which is a concentration more than 10,000 times higher than for DAS-1 and DAS-2.

To determine at which stage of the complement cascade blockade was occurring, a variation of the CH50 assay was carried out. Instead of measuring hemolysis, western blot analyses of red blood cell membranes were carried out to determine which serum complement proteins were converted into activated complement products that became attached to susceptible membranes. Such attachment only occurs up to the stage of blockade. At stages beyond the blockade, they remain unchanged in the serum. Results are shown in FIGS. 4 and 5. Undiluted human serum was treated for 30 min with DAS-1, DAS-2, or acetyl salicylic acid. Then antibody-conjugated red blood cells in an equal volume were added. The mixtures were incubated at 37° C. for 1 h. They were then treated with a lysis buffer followed by a loading buffer for western blots. Equal amounts of protein from each sample were loaded onto gels and separated by 10% SDS-PAGE. Following SDS-PAGE, proteins were transferred to a PVDF membrane. The membranes were then treated with various primary antibodies followed by labeled secondary antibodies using well established techniques. The list of antibodies that were utilized is shown in Table 1.

TABLE 1

Antibodies and peptides utilized for the experiments.

| Antibodies and proteins | Company | Dilution/final concentration |
|---|---|---|
| Polyclonal goat anti-sera to Human C1q | Quidel, San Diego, CA | 1/2,000 |
| Monoclonal mouse anti C3b Ab | Quidel, San Diego, CA | 1/2,000 |
| Monoclonal mouse anti C3d Ab | Quidel, San Diego, CA | 1/2,000 |
| Monoclonal mouse anti C4d Ab | Quidel, San Diego, CA | 1/2,000 |
| Monoclonal mouse anti C5/C5a Ab | Abcam, Cambridge, MA | 1/2,000 |
| Polyclonal Goat anti C6 Ab | Quidel, San Diego, CA | 1/2,000 |
| Polyclonal Goat anti C7 Ab | Quidel, San Diego, CA | 1/2,000 |
| Polyclonal Goat anti C8 Ab | Quidel, San Diego, CA | 1/2,000 |
| Polyclonal Goat anti C9 Ab | Quidel, San Diego, CA | 1/2,000 |
| Monoclonal mouse anti properdin Ab | Quidel, San Diego, CA | 1/2,000 for western blotting (FIG. 5) |
| Polyclonal Rabbit anti properdin Ab | Abcam, Cambridge, MA | 1/100 for removing human serum properdin (FIG. 4) |
| Monoclonal Factor Bb Ab | Quidel, San Diego, CA | 1/2,000 (FIG. 5) |
| Monoclonal Factor D Ab | Abcam, Cambridge, MA | 1/2,000 for western blotting (FIG. 5) and 1/100 for removing human serum factor D (FIG. 4) |
| HRP-Goat anti human IgG Ab | Sigma, St. Louis, MO | 1/2,000 |
| HRP-Mouse anti IgG Ab | Invitrogen, Carlsbad, CA | 1/2,000 |
| Human properdin protein | Quidel, San Diego, CA | 32 ng/mL (FIG. 6) |
| Human Factor D Protein | Quidel, San Diego, CA | 32 ng/mL (FIG. 6) |
| Human Factor B Protein | Sigma, St. Louis, MO | 32 ng/mL (FIG. 6) |
| Human C2 Protein | Sino Biologicals Inc., Beijing, China | 32 ng/mL (FIG. 6) |
| Human C3 Protein | Sigma, St. Louis, MO | 32 ng/mL (FIG. 6) |
| Human C4 Protein | Complement technology Inc., Tyler, TX | 32 ng/mL (FIG. 6) |
| Human C5 Protein | Complement technology Inc., Tyler, TX | 32 ng/mL (FIG. 6) |
| Human C6 Protein | Sigma, St. Louis, MO | 32 ng/mL (FIG. 6) |
| Human C7 Protein | Quidel, San Diego, CA | 32 ng/mL (FIG. 6) |
| Human C8 Protein | Sigma, St. Louis, MO | 32 ng/mL (FIG. 6) |
| Human C9 Protein | Sigma, St. Louis, MO | 32 ng/mL (FIG. 6) |
| C1 inhibitor | Quidel, San Diego, CA | 1.8 µg/mL (FIG. 5) |

Bands recognized by the antibodies were visualized by use of an enhanced chemiluminescence system and exposure to photographic film. For probing the same membrane with different antibodies, the membranes were treated with stripping buffer and then treated as before with a different primary antibody.

Figure 4A:
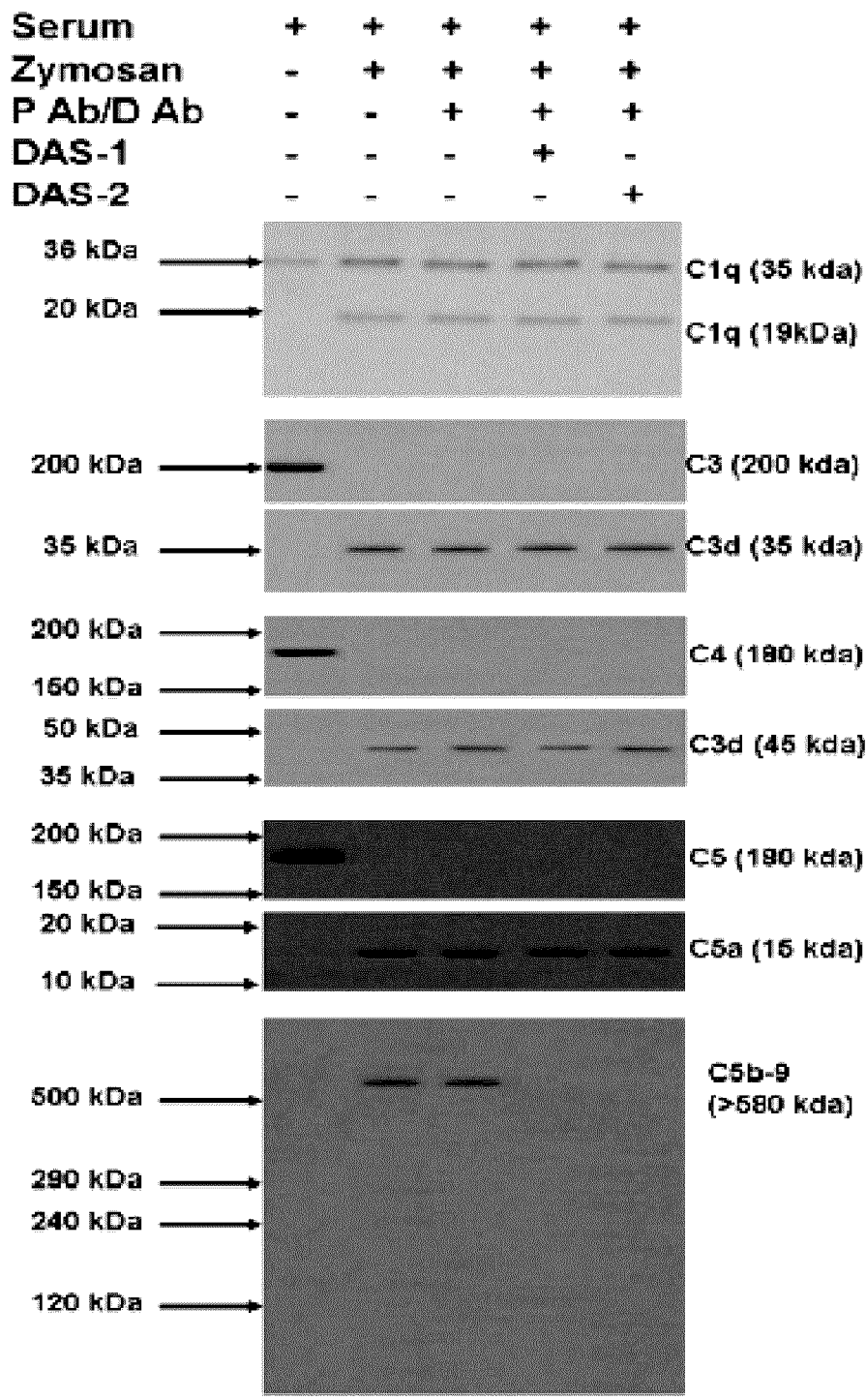
FIGS. 4A and 4B show Western blot analyses of human red blood cell membranes following exposure to zymogen-activated human serum. Only the classical pathway is activated since the alternative pathway is blocked by antibodies to properdin and Factor D.
Figure 5:
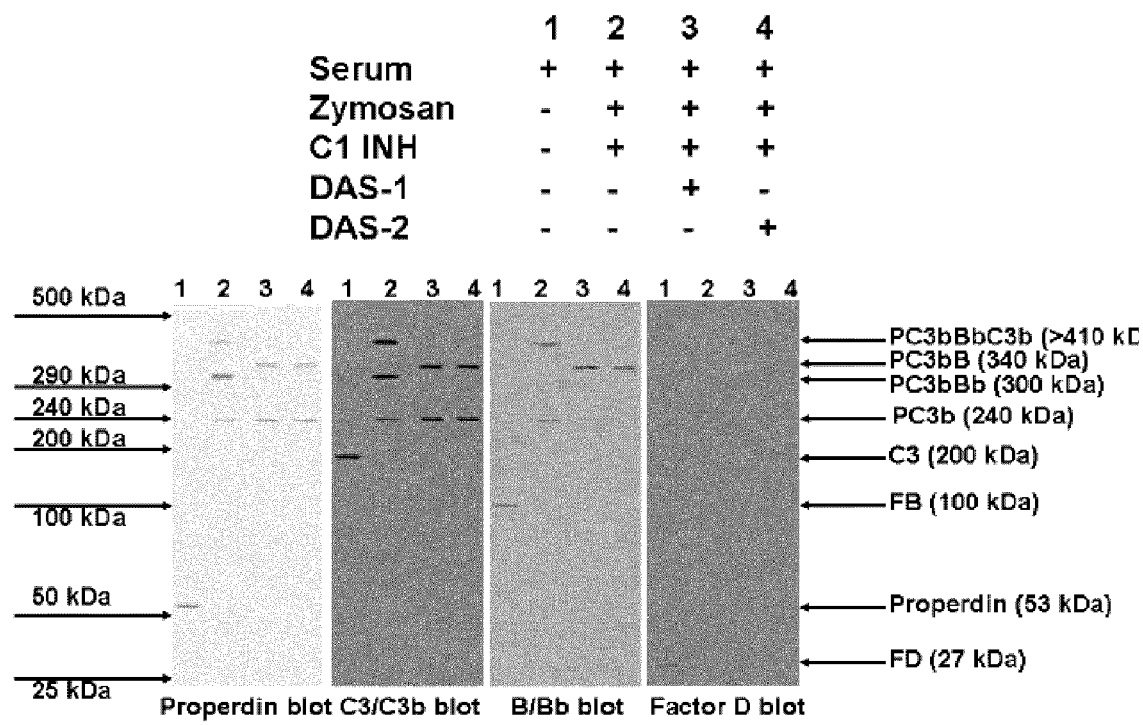
FIG. 5 shows Western blot analyses of human red blood cell membranes following exposure to zymogen-activated human serum where the classical pathway is blocked by C1 inhibitor.

Typical results for blockade of the classical pathway are shown in FIG. 4A. The left lane was loaded with serum only and shows that bands for C1q, C3, C4, and C5 were readily detected. The adjacent lane illustrates the effect of adding to the serum zymosan to activate complement, and antibodies to properdin and Factor D to block the alternative pathway.

Sensitized red blood cells then become hemolyzed by classical pathway attack. Native serum proteins are consumed and become incorporated into the red cell membranes. C1q was not metabolized, but the band was intensified due to its dissociation from the C1 complex. Native C3 was no longer detected because it had been cleaved, and the C3b fragment had become covalently attached to the membrane. Its degradation product C3d was detected. C4 was no longer detected because it had similarly been cleaved and the C4b fragment attached to the membrane and metabolized into its degradation product C4d. This fragment was also detected. C5 was cleaved and a band for the C5a product detected. Finally, the C5b-9 membrane attack complex, which had formed on the red cell membrane causing its hemolysis, was detected.

The next two lanes show the effects of incubation in the presence of DAS-1, DAS-2. Identical bands for the opsonization steps were detected, but the red cells were not hemolyzed and the membrane attack complex was not detected. This establishes that the block provided by DAS-1 and DAS-2 was at the MAC assembly stage.

Figure 4B:
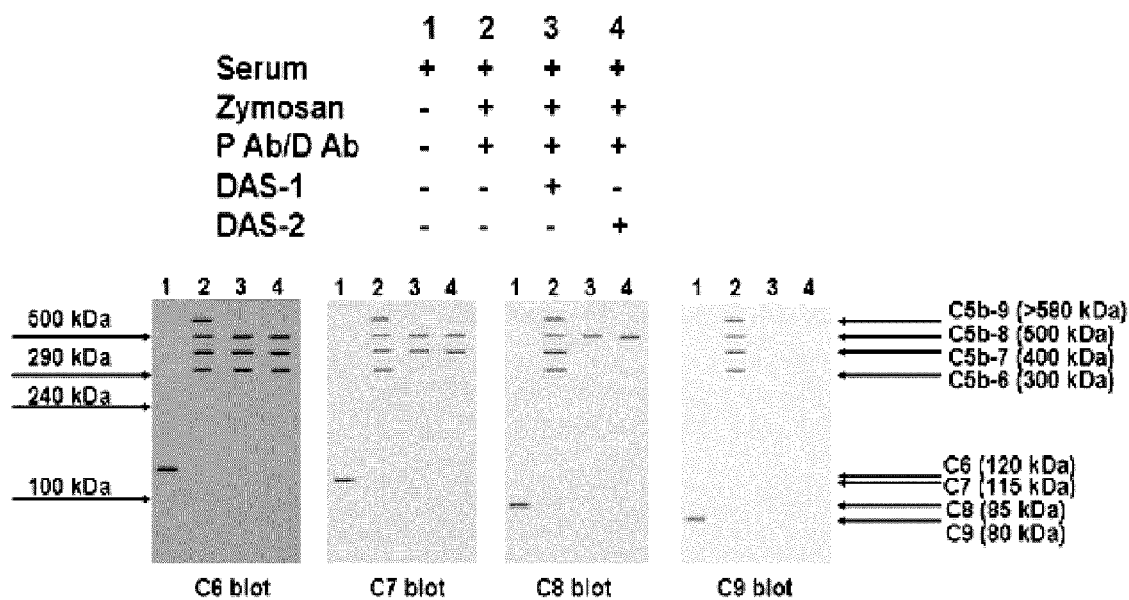

To determine at which stage of assembly the membrane attack complex was being blocked, additional western blots were carried out and the membranes probed with antibodies to C6, C7, C8 and C9. The results are shown in FIG. 4B. Lane 1 for human serum alone shows that C6, C7, C8 and C9 were readily detected in the untreated serum. Lane 2 shows that in unprotected red blood cells that have become hemolyzed by complement attack, these antibodies detected only C5b-9, the fully formed membrane attack complex. Lane 3, in which the cells have been protected by DAS-1, shows that the membrane attack complex does not fully form but becomes arrested at the C8 stage. The C6 antibody detected C5b6, C5b67, and C5b678. The C7 antibody detected C5b67 and C5b678, while the C8 antibody detected C5b678. Lane 4 in which the cells have been protected by DAS-2 shows the same results as in lane 3. These data establish that DAS-1 and DAS-2 arrest formation of the membrane attack complex at the stage where C9 attaches to C5b678. Since C9(n) is required for creating the membrane destroying holes, this blockade is highly specific to preventing C9 attachment.

To determine the effects of DAS-1 and DAS-2 on the alternative pathway, further experiments were carried out as shown in FIG. 5. Lane 1 in the western blots shows the bands detected in normal serum; lane 2 the effects when normal serum (15 fold dilution) was activated with zymosan with the classical pathway being blocked with C1 inhibitor (1.8 micrograms/mL); lane 3 the effects of adding DAS-1; and lane 4 the effects of adding DAS-2 (both at 1 microM). To these mixtures human RBCs ($5 \times 10^9$) were added. The mixtures were incubated for 1 h at 37° C. and centrifuged at 5,000 rpm for 10 mM. The pellets were washed two times with Hank's balanced salt solution (HBSS) and treated with sample loading buffer for SDS-PAGE and immunoblotting. The buffer consisted of 50 mM Tris (pH 6.8), 0.1% SDS, 0.1% bromophenol blue and 10% glycerol. To preserve the molecular complexes that had formed, mild conditions for SDS-PAGE were followed. The sample loading buffer used was 50 mM Tris (pH 6.8), 1% SDS, 0.1% bromophenol blue and 10% glycerol and 2% beta-mercaptoethanol.

FIG. 5 shows the results when western blots were developed with monoclonal antibodies to properdin (1/2,000), C3b (1/2,000), Factor B/Bb (1/2,000) and Factor D (1/2,000) respectively. Lane 1 in each blot shows that the native proteins were detected in untreated serum. Lane 2 shows that in serum that has been activated by zymosan in the presence of C1 inhibitor, similar bands on RBC membranes were detected by antibodies to properdin, C3b and Factor B/Bb corresponding in MW to PC3b (~240 kDa), PC3bB (~340 kDa), PC3bBb (~300 kDa) and PC3bBbC3b (>410 kDa). These data show that C3 convertase and C5 convertase were present on the membranes. However an independent band for C3b was not detected. This result indicates that C3b required properdin to bind and direct its binding to the erythrocyte membranes. The antibody to Factor D did not detect any bands for Factor D, indicating that Factor D did not form any SDS stable complexes on the membranes. Lanes 3 and 4 show the results obtained in the presence of 1 microM of DAS-1 or DAS-2. Bands for PC3bBb and PC3bBbC3b did not form. Instead, strong bands for the earlier steps of PC3b and PC3bB appeared. These results indicate that arrest of activation occurred at the stage where PC3bB becomes cleaved by Factor D to form the C3 convertase enzyme. They provide further evidence that Factor D does not form a stable bond attached to membranes but remains in the serum.

Figure 6A:
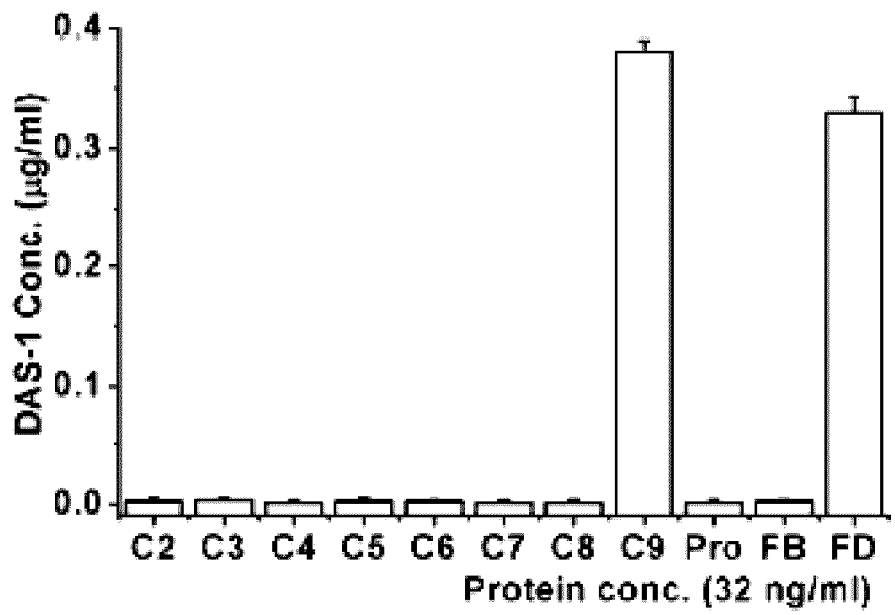
FIGS. 6A and 6B are graphs showing specific binding of DAS-1 and DAS-2 to C9 and Factor D, but not to C2, C3, C4, C5, C6, C7, C8, Properdin, and Factor B.
Figure 6B:
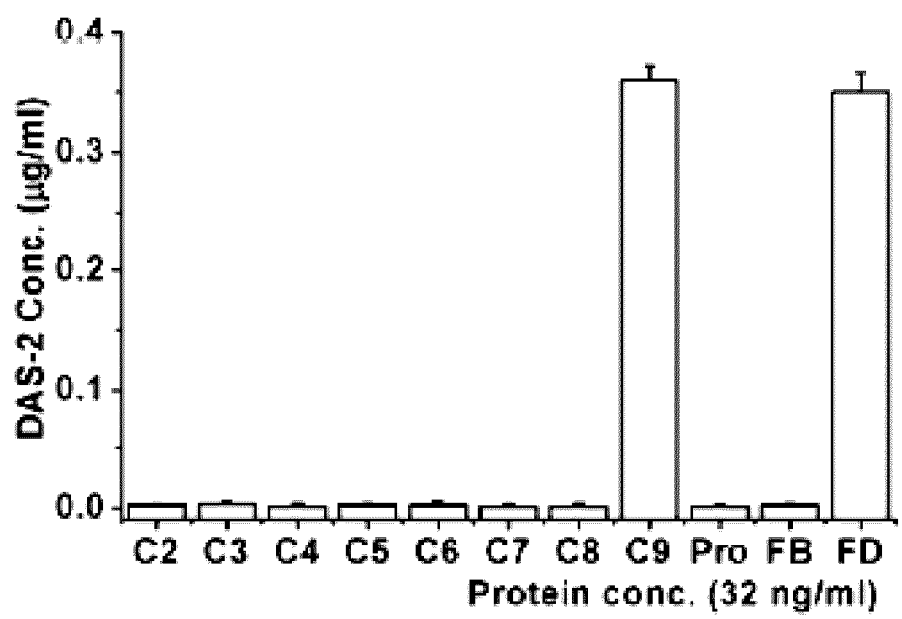

The next set of experiments directly tested the binding of DAS-1 and DAS-2 to properdin, Factor D and complement proteins. These proteins were immobilized on microwell plates in a concentration range of 1-32 ng/mL. DAS-1 and DAS-2 were then added at a concentration of 100 microgm/mL and the solutions incubated as previously described. DAS-1 and DAS-2 binding to the proteins was then assayed according to a previously published fluorometric method except that the excitation frequency was 290 nM and the emission frequency 348 nM. FIG. 6A shows the results for DAS-1 and FIG. 6B identical results for DAS-2. DAS-1 and DAS-2 bound strongly to Factor D and C9. Such binding explains why DAS-1 and DAS-2 block the alternative pathway at the stage where Factor D cleaves PC3B to form PC3Bb, and both the classical and alternative pathways at the stage where C9 adds to C5b678. However, other complement proteins such as C2, C3, C4, C5, C6, C7, C8 and Factor B (32 ng/mL each) did not bind to DAS-1 or DAS-2. There was no binding of DAS-1 or DAS-2 to properdin and only background fluorescence was observed. This result is consistent with observations that properdin binding to erythrocyte membranes is unaffected by DAS-1 and DAS-2.

Applicability of the Invention to the Treatment of Chronic Inflammatory Diseases The invention relate to methods of preventing and/or treating complement-mediated chronic inflammatory diseases by systemic, including oral, administration of acetyl salicylic acid dimers such as DAS-1 and DAS-2 and their isomers.

According to one embodiment, the compounds and compositions provided herein can be used to prevent and/or treat paroxysmal nocturnal hemoglobinemia. Paroxysmal nocturnal hemoglobinemia results from a clonal deficiency in erythrocytes of the X chromosome gene PIGA. As a consequence, the glycosal phosphatidylinositol moiety necessary for anchoring membrane proteins such as CD 55 and CD 59 is non-functional. Erythrocytes and platelets lack the capacity to restrict cell-surface activation of the alternative pathway. Patients are subject to fatal thrombotic and hemolytic attacks. A treatment which is partially effective is to administer at biweekly intervals the monoclonal antibody eculizumab, which blocks C5 cleavage, preventing synthesis of the membrane attack complex. However this treatment is less than satisfactory being effective in preventing transfusions in only 49% of patients (Hillmen et al. 2006). A probable reason is that it does not block C3 convertase activity. C3 convertase activity is unregulated due to the CD 55 deficiency (Parker 2002). DAS-1, DAS-2 and their isomers are expected to prevent and/or treat paroxysmal nocturnal hemoglobinemia as these compounds both prevent formation of the membrane attack complex and block C3 convertase activity.

According to one embodiment, the compounds and compositions provided herein can be used to prevent and/or treat atypical hemolytic uremia syndrome. Atypical hemolytic uremia syndrome is a chronic, life-threatening, disease caused by self-attack of the complement system. It is mainly due to mutations in Factor H, which then fails to protect cells from alternative pathway activation. Damage then occurs in endothelial cells, erythrocytes and kidney glomeruli frequently leading to kidney failure (Jokiranta et al. 2006). DAS-1 and DAS-2 and their isomers are expected to prevent and/or treat atypical hemolytic uremia syndrome as these compounds inhibit the complement system, including the alternative pathway, by blocking C3 convertase activity and preventing formation of the membrane attach complex.

According to one embodiment, the compounds and compositions provided herein can be used to prevent and/or treat rheumatoid arthritis. There is strong evidence that both the classical and alternative pathways of complement are pathologically activated in rheumatoid arthritis (Okroj et al. 2007). The arthritic joint contains proteins capable of activating complement as well as proteins signifying that both the classical and alternative pathways have been activated. In mouse models of rheumatoid arthritis, resistance can be achieved by deletion of C3, C5, or Factor B (Okroj et al. 2007). These data indicate that DAS-1 and DAS-2 and their isomers should be effective in preventing and/or treating rheumatoid arthritis.

According to one embodiment, the compounds and compositions provided herein can be used to prevent and/or treat multiple sclerosis. Multiple sclerosis is a relapsing-remitting disease characterized by inflammation of the white matter of brain. Specific antibodies have been detected which target myelin antigens indicating that it is an autoimmune disorder (Compston et al., 1989). Complement will be activated in this process indicating the appropriateness of DAS-1 and DAS-2 and their isomers in prophylaxis and/or therapy.

According to one embodiment, the compounds and compositions provided herein can be used to prevent and/or treat malaria infection. Malaria is a prevalent disease in Africa and south East Asia, resulting in an estimated 650,000 deaths per year. The infective agent, plasmodium falciparum, transmitted by mosquitos, produces enhanced complement activation in humans and susceptible animals. IgG and C3bBb complexes have been identified on erythrocytes of infected humans indicating damage caused by activation of both the classical and alternative pathways (Silver et al. 2010). Accordingly, prevention and/or treatment with DAS-1 and DAS-2 and their isomers should be effective.

According to one embodiment, the compounds and compositions provided herein can be used to prevent and/or treat Alzheimer's disease. It has long been known that beta amyloid protein deposits in brain, which are believed to be the primary cause of the disease, can be identified by the opsonizing components of complement. It was demonstrated that this was due to C1q binding to beta amyloid protein (Rogers et al., 1992). It was also demonstrated that the membrane attack complex of complement decorated damaged neurites in the vicinity of the deposits, indicating self-damage by the complement system (McGeer et al., 1989). Taken together, these data illustrate that the opsonizing aspects of complement need to be preserved so that phagocytosis of the beta amyloid deposits can occur, while the membrane attack complex needs to be selectively blocked so that self-damage to host neurons can be eliminated. For these reasons, DAS-1 and DAS-2 and their isomers should be an effective prophylactic and/or treatment for Alzheimer disease.

According to one embodiment, the compounds and compositions provided herein can be used to prevent and/or treat age-related macular degeneration. Opsonizing components of complement have been identified in association with drusen, which are the extracellular deposits associated with the disease. The membrane attack complex has been found near the degenerating retinal pigment epithelial cells. Genetic analyses have revealed that polymorphisms in Factor H, Complement Factor B, and C3 all significantly influence the risk of suffering from age-related macular degeneration (Anderson et al., 2010). These data illustrate that the opsonizing aspects of complement need to be preserved so that phagocytosis of drusen can occur, while the membrane attack complex needs to be selectively blocked so that self-damage to retinal pigment epithelial cells can be eliminated. For these reasons, DAS-1 and DAS-2 and their isomers should be an effective prophylactic and/or treatment for age-related macular degeneration.

According to one embodiment, the compounds and compositions provided herein can be used to prevent and/or treat atherosclerosis. Atherosclerosis has not generally been considered to be exacerbated by the complement system. However the mRNA for C-reactive protein, a known activator of complement, is upregulated more than ten-fold in the area of atherosclerotic plaques. Plaque areas showing upregulation of C-reactive protein and the opsonization components of complement also demonstrate presence of the membrane attack complex (Yasojima et al., 2001). This is a further example of a common human degenerative condition where the membrane attack complex is present in a sterile situation and can therefore only damage host tissue. Again, the invention described here will preserve the desirable phagocytosis stimulating aspect of complement, while eliminating the self-damaging aspect of the membrane attack complex. For these reasons, DAS-1 and DAS-2 and their isomers should be an effective prophylactic and/or therapeutic treatment for atherosclerosis.

Applicability of the Invention to Inflammatory Skin Conditions

The invention also relate to methods of preventing and/or treating complement-mediated inflammatory skin conditions by topical application of acetyl salicylic acid dimers such as DAS-1 and DAS-2 and their isomers. In some embodiments the inflammatory skin conditions prevented and/or treated involve self-damaging complement activation. The term "inflammatory skin condition" as used herein refers to a skin or scalp condition characterized by one or more of irritation, blistering, redness, flaking, localized heat, pain, itching, and hair follicle damage/destruction.

According to one embodiment, the compounds and compositions provided herein can be used to prevent and/or treat androgenic alopecia (baldness) is the most common form of hair loss in males. It begins after puberty, with initial losses occurring in the temporal and occipital areas. It typically advances to baldness covering the entire scalp except for a rim extending around the peripheral regions. The cause is generally acknowledged to be a vulnerability of hair follicles in these areas to androgens, particularly dihydrotestosterone (DHT) (Garza et al. 2012). DHT interacts with the androgen receptor (AR) and it is high levels of this receptor that are presumed to create the vulnerability. The gene for AR is located at Xq11-Xq12. Genetic analyses have shown that variants in the receptor are associated with androgenic alopecia (Hillmer et al. 2005) and especially with a nearby gene named ectodysplasin receptor 2A (EDA2R) (Prodi et al. 2008). The product of the gene is a transmembrane protein of the tumor necrosis factor receptor super family. To date there is no explanation as to why activation of these receptors by DHT should result in disappearance of hair follicles in androgenic alopecia. Treatments for baldness have been developed based on reducing the substrate for these receptors, or increasing scalp circulation. Examples include minoxidil, an arterial dilator that has been used systemically and topically to promote hair growth. Finasteride, which blocks 5-alpha reductase conversion of testosterone to DHT, has been approved for hair loss. However, none of these approaches, or others that are totally empirical, provides any insight as to the mechanism that actually causes disappearance of hair follicles. Topical application of DAS-1 or DAS-2 and their isomers should be effective as prophylactic and/or therapeutic agents, by blocking complement attack of an enduring nature, thus permitting keratinocyte follicular re-growth.

According to one embodiment, the compounds and compositions provided herein can be used to prevent and/or treat acne. Acne is a skin condition which commonly commences during adolescence. It is characterized by seborrhea, comedones surrounded by erythematous areas, pustules, and nodules, especially of the facial area and upper torso. Many treatments have been tried but none are completely successful. The antioxidant benzoyl peroxide is commonly used, but it increases sensitivity to the sun. However Knor reports that in *P. acnes* humoral and cell mediated immunity as well as complement activation occurs. DAS-1 and DAS-2 and their isomers should be effective as prophylactic and/or therapeutic agents due to blockade of aberrant complement activation in this condition.

According to one embodiment, the compounds and compositions provided herein can be used to prevent and/or treat sunburn and thermal burns. Wan et al. reported a sharp increase in C3d in burn patients as well as Factor Ba, indicating activation of the alternative complement pathway. Fluctuations over a year suggested chronic inflammation was induced (Wan et al. 1998). Kang et al., in a study of patients with third-degree burns on more than 60% of the total body area, found complement consumption due to activation with survival being associated with recovery of this system (Kang et al 2003) Such burns should respond to treatment by DAS-1 and DAS-2 and their isomers due to their effectiveness in blocking aberrant complement activation.

According to one embodiment, the compounds and compositions provided herein can be used to prevent and/or treat atopic or allergic dermatitis. Atopic or allergic dermatitis occurs when the immune system of the skin attacks an allergen or other irritant (Seah P P et al. 1973; Triolo et al. 2003; Gober & Gaspari 2008). Keratinocytes can become damaged by this excessive attack. Through blockade of unwanted complement activation, DAS-1 and DAS-2 and their isomers should be effective prophylactic and/or therapeutic agents.

According to one embodiment, the compounds and compositions provided herein can be used to prevent and/or treat pemphigus. Pemphigus is a potentially fatal disorder where there is an autoimmune attack against desmoglien, the adhesive protein which forms the attachment of adjacent epidermal cells. Deposition of the membrane attack complex has been reported (Kawana S, et al. 1989). By blocking harmful complement activation, DAS-1 and DAS-2 and their isomers should be effective prophylactic and/or therapeutic agents.

Dermatitus herpetiformis is a condition which is characterized by an extremely itchy rash. It is linked to gluten intolerance and immune attack against the protein epidermal transglutaminase (Preisz et al. 2005). By inhibiting the alternative pathway at both the C3 convertase and C9 addition stages, DAS-1 and DAS-2 and their isomers should be effective prophylactic and/or therapeutic agents.

According to one embodiment, the compounds and compositions provided herein can be used to prevent and/or treat psoriasis. Psoriasis is a common skin condition which is characterized by an immune response (Triolo et al., 2003) which can be associated with rheumatoid arthritis (Ballanti et al., 2011). Currently there is no effective treatment. By inhibiting harmful complement activation, DAS-1 and DAS-2 and their isomers should be effective prophylactic and/or therapeutic agents.

According to one embodiment, the compounds and compositions provided herein can be used to prevent and/or treat discoid lupus erythematosis. Discoid lupus erythematosis is an autoimmune disorder which is highly exacerbated by sunlight. It is currently treated with topical steroids, indicative of the effectiveness of immune blockade. It has been reported that complement is activated even in non-lesioned skin of patients with systemic erythematosus (Alahlafi et al 2005). Deposition of C5b-9 was found in the epidermis of such patients (Magro et al 1996). By blocking harmful complement activation, DAS-1 and DAS-2 and their isomers should be effective prophylactic and/or therapeutic agents.

According to one embodiment, the compounds and compositions provided herein can be used to prevent and/or treat primary cicatricial alopecia (PCA). PCA is a skin disorder in which epithelial hair follicle stem cells are damaged or destroyed by inflammatory events (Harries et al. 2009). The affected stem cells reside in the outer root sheath of hair follicle bulges (Harries et al. 2009). This is an area hypothesized to be immunologically privileged (Meyer et al. 2008). Loss of such immunological privilege results in immune attack, so that hair follicles are replaced by scar tissue, with loss of hair (Harries et al. 2010). A mainstay of treatment is topical steroids. Since inflammation activates the complement system, by blocking this harmful complement activation, DAS-1 and DAS-2 and their isomers should be effective prophylactic and/or therapeutic agents.

According to one embodiment, the compounds and compositions provided herein can be used to prevent and/or treat seborrheic dermatitis and dandruff. Seborrheic dermatitis and dandruff are caused by an excessive loss of corneocytes from the outer layer of the epidermis (Scwartz et al., 2013). Immune dysfunction is suspected (Mills et al. 2012). The corneocytes adhere to each other creating flakes which are then shed. The pathogenesis appears to result from interactions between scalp skin, cutaneous microflora and the cutaneous immune system (Kerr et al. 2011). A proposed cause is *Malassezia* fungi (Gemmer et al. 2002). Increased levels of inflammatory markers are detected in biopsy specimens including IL-1beta and IL-1RA (Kerr et al. 2011). By blocking the consequent complement activation, DAS-1 and DAS-2 and their isomers should be effective prophylactic and/or therapeutic agents.

According to one embodiment, the compounds and compositions provided herein can be used to prevent and/or treat alopecia areata. Alopecia areata is a condition in which there is hair loss, usually from the scalp. It is characterized by a lymphocytic infiltration around vulnerable follicles, so that the hair growth disappears. The standard treatment is topical corticosteroids appropriate to an inflammatory response, or minodoxil, a capillary dilator which stimulates hair growth. However it has been reported that deposition of complement components C3, C5, and C9 are deposited in scalp hair follicles in subjects with alopecia areata (Igarashi et al 1981). By blocking this harmful complement activation which accompanies inflammation, DAS-1 and DAS-2 and their isomers should be effective prophylactic and/or therapeutic agents.

Systemic Modes of Delivery and Dosage

For complement-mediated chronic inflammatory and/or degenerative disorders such as paroxysmal nocturnal hemoglobinemia, age related macular degeneration, Alzheimer's disease, rheumatoid arthritis, atherosclerosis, atypical hemolytic uremia syndrome, multiple sclerosis, malaria infection, Pick's disease, Parkinson's disease, and neuromyelitis optica, the one or more dimers of acetyl salicylic acid such as DAS-1 and DAS-2 and their isomers may be administered orally or parenterally.

According to some embodiments, one or more dimers of acetyl salicylic acid may be administered orally in the form of tablets, capsules, pills, lozenge, granule, powder, suspension, emulsion, liquid, syrup, and the like. The one or more dimers may be combined with pharmaceutical acceptable carriers. In some embodiments the pharmaceutically acceptable carriers may prolong release, enhance effectiveness and/or decrease metabolism of the effective ingredients. Examples of pharmaceutically acceptable carriers include lactose, sucrose, mannitol, hydrogenated castor oil, sorbitol, dextrin, starch, stearic acid, propylene glycol, cellulose and other ingredients that are well known to those skilled in the art.

According to some embodiments, one or more dimers of acetyl salicylic acid may be administered parenterally, such as intravenously, subcutaneously, and through direct injection. The one or more dimers may be combined with pharmaceutical acceptable carriers such as distilled water, saline solution, balanced salt solutions, and other carriers that are well known to those skilled in the art. These modes may for example be desirable in situations where oral administration was not possible, or where high concentrations were necessary or desirable at some localized site.

Generally, therapeutically effective parenteral doses of the compounds of this invention for a patient will range from about 50 mg to 10 grams per day depending on the indication and needs of each particular subject.

Topical Modes of Delivery and Dosage

For complement-mediated inflammatory skin conditions such as androgenetic alopecia, thermal or ultraviolet burn, acne, atopic dermatitis, dandruff/seborrheic dermatitis, pemphigus, erythematosis, cicatricial alopecia and alopecia areata, the one or more dimers of acetyl salicylic acid such as DAS-1 and DAS-2 and their isomers may be administered topically. For topical application, the administration may be in the form of a spray, cream, ointment, gel, lotion, wash, shampoo, or lozenge, with the one more dimers being dissolved or suspended in an appropriate pharmaceutically acceptable vehicle. Examples of such vehicles are glycerine as a gel, aloe vera as an ointment, sodium lauryl sulfate plus cocamidopropyl betaine as a shampoo, and eucalyptus oil and pectin for a lozenge.

According to some embodiments, one or more acetyl salicylic acid dimers may be administered in the form of a skin care preparation, hair care preparation or a pharmaceutical composition formulated for application to affected areas of the skin or scalp of a patient. Such preparations or compositions may for example be formulated as a spray, gel, cream, lotion, stick, ointment, scrub, soap bar, tonic, roll-on formulation, sunscreen, shampoo or mousse wherein the one or more acetyl salicylic acid dimers is provided in a therapeutically effective amount together with at least one carrier so as to be capable of exerting a therapeutic effect on an inflammatory skin conditions on the patient's skin or scalp. The one or more acetyl salicylic acid dimers may be provided in such preparations or compositions at a concentration of 0.1 to 100 mg/mL, or 0.1 to 10 mg/mL, or 0.5 to 5 mg/mL, and may be topically applied on the affected area(s) one to five times daily for example.

In some embodiments, the preparations or compositions may also include one or more of surfactants, propellants, co-solvents, gelling agent, and other ingredients suitable for use in skin or hair care preparations of the type known in the art, such as petrolatum, waxes, oils plasticizers, preservatives, fragrances and the like.

In some embodiments, the preparations or compositions may be applied to the skin or scalp of a patient using bottles or containers (e.g. shampoos), tubes (e.g. gels, creams, ointments, lotions), pressurized canisters (e.g. sprays, mousses), pads, sticks, or "roll-on" applicators (e.g. gels, ointments).

In some embodiments, the preparations or compositions may be formulated to form a film over the skin or scalp, thus allowing controlled release and penetration of the one or more acetyl salicylic acid dimers such as DAS-1 and DAS-2 and their isomers into the affected areas.

In some embodiments, the one or more acetyl salicylic acid dimers may be provided at a concentration of 0.1 to 100 mg/mL, or 0.1 to 10 mg/mL, or 0.5 to 5 mg/mL, in an aqueous shampoo base comprising the surfactants sodium lauryl sulfate and cocamidopropyl betaine, for application to the scalp.

In some embodiments, the one or more acetyl salicylic acid dimers may be provided at a concentration of 0.1 to 100 mg/mL, or 0.1 to 10 mg/mL, or 0.5 to 5 mg/mL, in an ointment comprising glycerin, for application to the skin or scalp.

In some embodiments, the one or more acetyl salicylic acid dimers may be provided at a concentration of 0.1 to 100 mg/mL, or 0.1 to 10 mg/mL, or 0.5 to 5 mg/mL, in a gel comprising aloe vera, for application to the skin or scalp.

In some embodiments, the one or more acetyl salicylic acid dimers may be dissolved at a concentration of 0.1 to 100 mg/mL, or 0.1 to 10 mg/mL, or 0.5 to 5 mg/mL, in water and applied as a spray or other means to the affected skin or scalp area.

In some embodiments, the one or more acetyl salicylic acid dimers may be provided at a concentration of 0.1 to 100 mg/mL, or 0.1 to 10 mg/mL, or 0.5 to 5 mg/mL, in a sunscreen formulation comprising one or more known active sunscreen ingredients.

As those skilled in the art will appreciate, these methods of treatments and uses described herein are only examples of many conditions where the invention may be applied to produce prophylactic and/or therapeutic benefit. The inventors expect that the compounds described herein should be effective for all conditions complement-mediated disorders, including disorders in which C3 convertase is assembled on host cells and is causing significant self damage, and/or in which the membrane attack complex of complement is assembled on host cells and is causing significant self damage.

Specific pharmacological responses observed may vary according to and depending on the particular active compound and/or pharmaceutical acceptable carriers selected, as well as the type of formulation and mode of administration employed, and such expected variations or differences in the results are contemplated in accordance with practice of the present invention.

This application is intended to cover any variations, uses, or adaptations of the invention using its general principles. Further, this application is intended to cover such departures from the present disclosure as come within known or customary practice in the art to which this invention pertains and which fall within the limits of the appended claims. Accordingly, the scope of the claims should not be limited by the preferred embodiments set forth in the description, but should be given the broadest interpretation consistent with the description as a whole.

REFERENCES

The following references are related to the subject matter disclosed herein, and each such reference is hereby incorporated by reference herein in its entirety:

Alahlafi A, et al. 2005. Activation/inactivation of the classical pathway of complement in non-lesioned skin of patient with systemic lupus erythematosus, J Cutan Pathol 32(8): 537-540

Anderson, D. H., et al. 2010. The pivotal role of the complement system in aging and age-related macular degeneration: hypothesis revisited. Prog. Ret. Eye Res. 29, 95-112.

Ballanti E, et al. 2011. Role of the complement system in rheumatoid arthritis and psoriatic arthritis: relationship with anti-TNF inhibitors. Autoimmun Rev 10(10), 617-623.

Compston D A S, et al. 1989 Immunocytochemical localization of the terminal complement complex in multiple sclerosis. Neuropathol App Neurobiol. 15, 307-316.

Garza L A, et al. 2012. Prostaglandin D2 inhibits hair growth and is elevated in bald scalp of men with androgenic alopecia. Sci Transl Med 4 (126).

Gober M D, Gaspari A A 2008. Allergic contact dermatitis. Curr. Dir. Autoimmun. 10, 1-26.

Harries M J, Meyer K C, Paus R. 2009. Hair loss as a result of cutaneous autoimmunity: frontiers in the immunopathogenesis of primary cicatricial alopecia. Autoimmune Rev. 8(6), 478-483.

Harries M J, et al. 2010. Does collapse of immune privilege in the hair-follicle bulge play a role in the pathogenesis of primary cicatricial alopecia? Clin. Exp. Dermatol. 35(6), 637-644.

Hillmen P, et al. 2006. The complement inhibitor eculizumab in paroxysmal nocturnal hemoglobinuria. N. Engl. J. Med. 355, 1233-1243.

Hillmer A M, et al. 2005. Genetic variation in the human androgenic receptor gene is the major determinant of common early-onset androgenic alopecia. Am. J. Hum. Gen., 77(1), 140-148.

Igarashi R, et al. 1981 Immunofluorescence studies on complement components in the hair follicles of normal scalp affected by alopecia areata. Acta Dem Venereol 61(2): 131-135.

Jokiranta T S, et al. 2006. Structure of complement factor H carboxyl terminus reveals molecular basis of atypical haemolytic uremic syndrome. EMBO Journal 25; 1784-1794.

Kang H J, et al. 2003. Change of complement system predicts the outcome of patients with severe thermal injury. J Burn Care Rehabil 24(3): 148-153.

Kawana S, et al. 1989. Deposition of the membrane attack complex of complement in pemphigus vulgaris and pemphigus foliaceus skin. J Investig Dermatol 92(4), 588-592.

Kerr K, et al. 2011. Epidermal changes are associated with symptomatic resolution of dandruff: biomarkers of scalp health. Int J Dermatol 50(1), 102-113.

Knor T 2005. The pathogenesis of acne. Acta Dermatovenerol Croa. 13(1): 44-49.

McGeer P L, et al. 1989. Activation of the classical complement pathway in brain tissue of Alzheimer patients. Neuroscience Letters 107, 341-346.

Magro C M, et al. 1996. The use of antibody to C5b-9 in the subclassification of lupus erythematosus. Br J Dermatol 134(5): 855-862.

Meyer K C, et al. 2008. Evidence that the bulge region is a site of relative immune privilege in human hair follicles. Br J Dermatol. 159(5), 1077-1085.

Mills K J, et al. 2012. Dandruff/seborrhoeic dermatitis is characterized by an inflammatory genomic signature and possible immune dysfunction: transcriptional analysis of the condition and treatment effects of zinc pyrithione. Br J Dermatol. 166 Suppl 2, 33-40.

Okroj M, et al. 2007. Rheumatoid arthritis and the complement system. Ann. Med. 39, 517-530.

Parker C J, 2002. Historical aspects of paroxysmal nocturnal haemoglobinemia. Br J Haematol. 117: 3-22.

Prodi D A, et al. 2008. EDA2R is associated with androgenic alopecia. J Inves Derm. 128, 2268-2270.

Rogers J, et al. 1992. Complement activation by b-amyloid in Alzheimer disease. PNAS USA 89; 10016-20.

Seah P P, et al. 1973. Alternate-pathway complement fixation by IgA in the skin of dermatitis herpetiformis. The Lancet Jul. 28, 1973, 175-177.

Schwartz J R, et al. 2013. A comprehensive pathophysiology of dandruff and seborrheic dermatitis-towards a more precise definition of scalp health. Acta Derm Venereol 93(2), 131-137.

Silver K L, Higgins S J, McDonald C R, Kain K C. 2010. Complement driven innate immune response to malaria: fuelling severe malarial diseases. Cell Microbiol. 2010 August; 12(8):1036-45

Triolo G, et al. 2003. Impaired expression of erythrocyte glycol-phosphotidylinosotol-anchored membrane CD59 in patients with psoriatic arthritis. Relation to terminal complement pathway activation. Clin Exp Rheumatol 21, 225-228.

Wan K C, et al. 1998. A longitudinal study of C3, C3d, and Factor Ba in burn patients in Hong Kong Chinese. Burns 24(3): 241-244.

Yasojima K, et al. 2001. Generation of C-reactive protein and complement components in atherosclerotic plaques. Am J Pathol 158; 1038-1051.

The invention claimed is:
1. A compound selected from the group consisting of
5,5'-methylenebis(2-acetoxybenzoic acid),
2-acetoxy-3-(4-acetoxy-3-carboxybenzyl)benzoic acid,
2-acetoxy-3-(3-acetoxy-4-carboxybenzyl)benzoic acid,
2-acetoxy-4-(4-acetoxy-3-carboxybenzyl)benzoic acid,
3,3'-methylenebis(2-acetoxybenzoic acid),
4,4'-methylenebis(2-acetoxybenzoic acid),
and salts thereof.
2. A compound according to claim 1, which is 5,5'-methylenebis(2-acetoxybenzoic acid), or a salt thereof.

3. A pharmaceutical composition comprising:
  a. a compound selected from the group consisting of:
     i. 5,5'-methylenebis(2-acetoxybenzoic acid),
     ii. 2-acetoxy-3-(4-acetoxy-3-carboxybenzyl)benzoic acid,
     iii. 2-acetoxy-3-(3-acetoxy-4-carboxybenzyl)benzoic acid,
     iv. 2-acetoxy-4-(4-acetoxy-3-carboxybenzyl)benzoic acid,
     v. 3,3'-methylenebis(2-acetoxybenzoic acid), and
     vi. 4,4'-methylenebis(2-acetoxybenzoic acid); and
  b. a pharmaceutically acceptable carrier.

4. A method of treating a complement-mediated disorder in a mammal, the method comprising administering to the mammal a pharmaceutical composition according to claim 3, wherein the complement-mediated disorder is selected from the group consisting of paroxysmal nocturnal hemoglobinemia, age-related macular degeneration, Alzheimer's disease, rheumatoid arthritis, atherosclerosis, atypical hemolytic uremia syndrome, multiple sclerosis, malaria, inflammatory skin disorder, androgenetic alopecia, thermal or ultraviolet burn, acne, atopic dermatitis, dandruff/seborrheic dermatitis, pemphigus, erythematosus and cicatricial alopecia.

* * * * *